US00PP08243P

United States Patent [19]

Van Der Knaap

[11] Patent Number: Plant 8,243

[45] Date of Patent: Jun. 1, 1993

[54] CHRYSANTHEMUM PLANT NAMED QUIET EYES

[75] Inventor: Jack Van Der Knaap, De Lier, Netherlands

[73] Assignee: Fides Beheer B.V., De Lier, Netherlands

[21] Appl. No.: 712,052

[22] Filed: Jun. 7, 1991

[51] Int. Cl.[5] ..... A01H 5/00

[52] U.S. Cl. ..... Plt./74.1

[58] Field of Search ..... Plt./74, 74.1, 82.4

[56] References Cited

U.S. PATENT DOCUMENTS

P.P. 3,455 1/1974 Machin et al. ..... Plt. 74
P.P. 4,623 1/1981 Jessel, Jr. et al. ..... Plt. 74
P.P. 4,692 4/1981 Meek et al. ..... Plt. 74
P.P. 5,815 12/1986 Hoek et al. ..... Plt. 74
P.P. 6,059 12/1987 Duffett et al. ..... Plt. 74
P.P. 6,900 7/1989 VandenBerg ..... Plt. 74

*Primary Examiner*—Howard J. Locker
*Attorney, Agent, or Firm*—Burns, Doane, Swecker & Mathis

[57] ABSTRACT

A new and distinct variety of Chrysanthemum plant. The new plant is characterized by its flat capitulum form, daisy capitulum type, lavender ray floret color, yellow disc floret color graduating to a large green eye, a diameter across the face of capitulum of 8.0 to 10.0 cm, upright to spreading branching pattern with ca. 3–4 breaks after a single pinch, a flowering response of 57 to 63 days from the start of short days, and a plant height for a 6.5 inch (16.5 cm) pot of about 40 cm with 1–2 applications of B-9 at 2500 ppm.

1 Drawing Sheet

BACKGROUND

1. The Field of the Invention

This invention relates to Chrysanthemum plants. More particularly, the present invention comprises a new and distinct cultivar of Chrysanthemum plant, botanically known as *Dendranthema grandiflora* and hereinafter referred to by the cultivar name "Quiet Eyes."

2. Background of the New Plant

Quiet Eyes, identified as 87.2754, was originated from a cross made by Jack Van Der Knapp in a controlled breeding program at De Lier, Holland in 1986.

The female parent of Quiet Eyes was Pall Mall (non-patented in the United States), and the male parent was Delta (U.S. Plant Pat. No. 5,815).

Quiet Eyes was discovered and selected as one flowering plant within the progeny of the stated cross by jack Van Deer Knaap in October of 1987 in a controlled environment at De Lier, Holland.

The first asexual reproduction of Quiet Eyes was accomplished when vegetative cuttings were taken in December of 1987 in a controlled environment at De Lier, Holland by technicians working under the direction and supervision of Jack Van Der Knaap.

SUMMARY OF THE INVENTION

The basic characteristics which have been repeatedly observed in Quiet Eyes and which, in combination, distinguish this Chrysanthemum plant over related known varieties and its antecedents are:

1. Flat capitulum form.
2. Daisy capitulum type.
3. Lavender ray floret color.
4. Yellow disc floret color graduating to a large green eye.
5. Diameter across face of capitulum 8.0 to 10.0 cm.
6. Branching pattern is upright to spreading with ca. 3–4 breaks after a single pinch.

7. Flowering response is 57 to 63 days from the start of short days.
8. Plant height of a 6.5 inch (16.5 cm) pot is about 40 cm with 1–2 applications of B-9 at 2500 ppm.

Horticultural examination of controlled flowerings of successive plantings has shown that the combination of characteristics and distinctions as herein disclosed for Quiet Eyes are firmly fixed and are retained through successive generations of asexual reproduction.

DETAILED DESCRIPTION OF THE NEW PLANT

Figure 1:
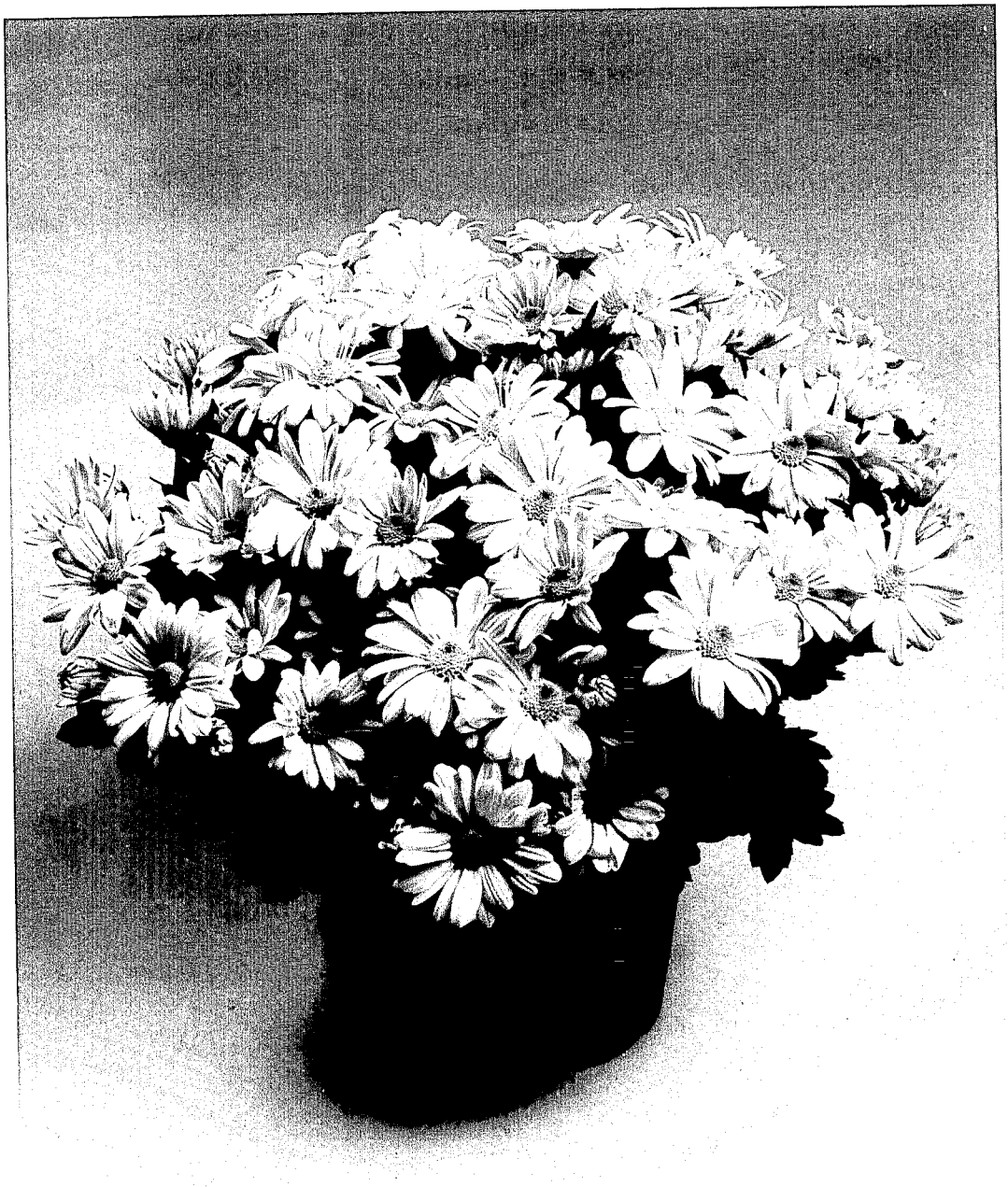
FIG. 1 is a photographic print in full color showing typical inflorescence and leaf characteristics of Quiet Eyes grown as a pinched spray pot mum with 5 cuttings in a 6.5 inch (16.5 cm) pot, the colors being depicted as nearly true as it is reasonably possible to make the same in a color photograph of this character.

Quiet Eyes has not been observed under all possible environmental conditions. The phenotype may vary significantly with variations in environment such as temperature, light intensity, and day length.

The following is a detailed description of Quiet Eyes, with color terminology in accordance with *The Royal Horticulture Society Colour Chart*, except where general color terms of ordinary dictionary significance are obvious. The following observations, measurements and comparisons were made of plants grown at Nipomo, Calif. in controlled environments. Unrooted cuttings were directly stuck into 6.5 inch (16.5 cm) pots and grown in a controlled environment under the natural temperature and day length prevailing during October through December of 1990.

Classification:

*Botanical.*—*Dendranthema grandiflora* cv. Quiet Eyes.

*Commercial.*—Daisy to be grown as a spray pot.

INFLORESCENCE

A. Capitulum:
- *Form.*—Flat.
- *Type.*—Daisy.
- *Diameter across face.*—8–10 cm when fully opened.

B. Corolla of ray florets:
- *Color (general tonality from a distance of three meters).*—Lavender pink with a lemon yellow disc graduating to a green eye.
- *Color.*—Front: 75 B. Back: 75 D.
- *Shape.*—Oblong.

C. Corolla of disc florets:
- *Color.*—Lemon Yellow 1 A. Graduating to a large green eye of 143 A.

D. Reproductive organs:
- *Androecium.*—Present on disc florets only; insignificant.
- *Gynoecium.*—Present on both ray and disc florets; insignificant.

PLANT

A. General appearance:
- *Height.*—When grown in 6.5 inch (16.5 cm) pots with 1–2 applications of B-9, the total plant height including the pot will be ca. 40 cm.
- *Branching pattern.*—Upright to spreading with 3–4 breaks after the pinch.

B. Foliage:
- *Color (upper surface).*—147 A.
- *Color (lower surface).*—147 B.

*Shape.*—See FIG. 1 Up to 10 cm long. Up to 5.5 cm wide.

Quiet Eyes can be well distinguished from other commercial Chrysanthemum cultivars, including Autumn Eyes (U.S. plant patent application Ser. No. 712,334 filed Jun. 7, 1991), Dark Eyes (U.S. plant patent application Ser. No. 712,903 filed Jun. 7, 1991), Definite Eyes (U.S. plant patent application Ser. No. 712,086 filed Jun. 7, 1991), Tara (U.S. Plant Pat. No. 6,313), and Vibrant Eyes (U.S. plant patent application Ser. No. 712,901 filed Jun. 7, 1991). See in this regard the data presented in Table A hereinafter. Also, the blossom coloration of Quiet Eyes can be readily distinguished from Coral Marble (U.S. Plant Pat. No. 3,455), Citation (U.S. Plant Pat. No. 4,623), Nova (U.S. Plant Pat. No. 4,692), Delta (U.S. Plant Pat. No. 5,815), Adorn (U.S. Plant Pat. No. 6,059) and Apto (U.S. Plant Pat. No. 6,900), as described in the respective U.S. Plant Patents.

Similar traits to the other above-mentioned "Eye" varieties are capitulum form, branching pattern, and the distinctly contrasting center of the disc. However, each "Eye" variety varies in color of the disc and ray florets, making each a unique and different cultivar.

Similar traits to Tara are capitulum form, and breaks/pinch. Quiet Eyes, generally has more disc florets and more ray florets per flower, and the ray florets are generally longer by an average of 1 cm. Quiet Eyes is approximately 4–7 days slower, and has fewer flowers per break than Tara. The coloration of the petals is very different between Tara and Quiet Eyes.

TABLE A

| Characteristic | Autumn Eyes | Dark Eyes | Definite Eyes |
|---|---|---|---|
| capitulum form | flat | flat | flat |
| capitulum type | anemone | anemone | anemone |
| diameter across face | ca. 3.4 cm | ca. 3.5–6.0 cm | 4.0–7.0 cm |
| branching pattern | upright | spreading | upright and spreading |
| breaks/pinch | ca. 4.0 | 4–7 | 3–5 |
| height in 6.5 in. (16.5 cm) pot with 1–2 applications of B-9 | 30–40 cm | ca. 40 cm | 40–52 cm |
| disc floret color | golden 11 A tipped with dark maroon 59 A; eye is dark maroon 59 A | medium lavender 75 C graduating to a very dark eye of 77 A; tube 75 C | 56 C on the outer petals graduating to a dark purple eye of 59 A |
| no. disc florets | ca. 171 | ca. 145 | ca. 255 |
| length disc florets | ca. 1.0 cm long | 1.0–1.5 cm long | up to 2 cm long |
| ray floret color | front: golden yellow 11 A back: pale yellow 11 B | front: 75 C back: 75 C with a 77 B stripe down the center | front: 69 D back: some 70 C |
| no. ray florets | ca. 22 | 24–27 | average of 27.3 |
| shape ray florets | oblong with rounded to flat tip | oblong with rounded tip | elliptic |
| length ray florets | 1.0–1.5 cm long | up to 2.5 cm long | up to 4 cm long |
| width ray florets | 0.3–0.5 cm wide | up to 0.75 cm wide | up to 1.0 cm wide |
| no. flowers/break | ca. 9.6 | average of 5.16 | average of 5.3 |
| leaf color | front: 147 A back: 147 B | front: 147 A back: 147 B | front: 147 A back: 147 B |
| leaf length | ca. 7.5 cm long | up to 8 cm long | up to 6 cm long |
| leaf width | ca. 5.0 cm wide | up to 4.5 cm wide | up to 4 cm wide |
| response time | 8.5 weeks | 8.5 weeks | 8.5 weeks |

| Characteristic | Quiet Eyes | Tara | Vibrant Eyes |
|---|---|---|---|
| capitulum form | flat | flat | flat fresh; puffy rounded old |
| capitulum type | daisy | anemone | anemone |
| diameter across face | 8–10 cm | 5.0–6.5 cm | 3–4 cm |
| branching pattern | spreading | spreading | upright to spreading |
| breaks/pinch | 3–4 | 3–5 | 4–5 |
| height in 6.5 in. (16.5 cm) pot with 1–2 applications of B-9 | ca. 40 cm | ca. 37 cm | 42–52 cm |
| disc floret color | lemon yellow 1 A graduating to a large green eye of 143 A | lemon yellow 10 A | from 155 D graduating toward a dark purple eye of 77 A |
| no. disc florets | ca. 200 | 70–120 | ca. 125 |
| length disc florets | 1.3 cm long | up to 1.5 cm long | ca. 1 cm long |
| ray floret color | front: 75 B back: 75 D | front: 155 A back: 155 D | light pink to white; front: 155 A back: 155 B bright green ovary |
| no. ray florets | 20–24 | 15–17 | ca. 22 |
| shape ray florets | oblong | elliptic | oval with rounded tip |
| length ray florets | up to 4 cm long | up to 3 cm long | up to 1.7 cm long |
| width ray | up to 1.5 cm | up to 1 cm wide | up to 0.5 cm |

TABLE A-continued

| | | | |
|---|---|---|---|
| florets | wide | | wide |
| no. flowers/ break | ca. 5.2 | ca. 11.3 | ca. 8.4 |
| leaf color | front: 147 A<br>back: 147 B | front: 147 A<br>back: 147 B | front: 147 A<br>back: 147 B |
| leaf length | up to 10 cm long | up to 9 cm long | up to 5.0 cm long |
| leaf width | up to 5.5 cm wide | up to 5 cm wide | up to 3.0 cm wide |
| response time | 8.2 weeks | 8.0 weeks | 8.0 weeks |

I claim:

1. A new and distinct variety of Chrysanthemum plant, substantially as herein described and illustrated.

* * * * *